April 3, 1951 E. S. BOERNER Plant Pat. 1,011
ROSE PLANT
Filed Feb. 21, 1950
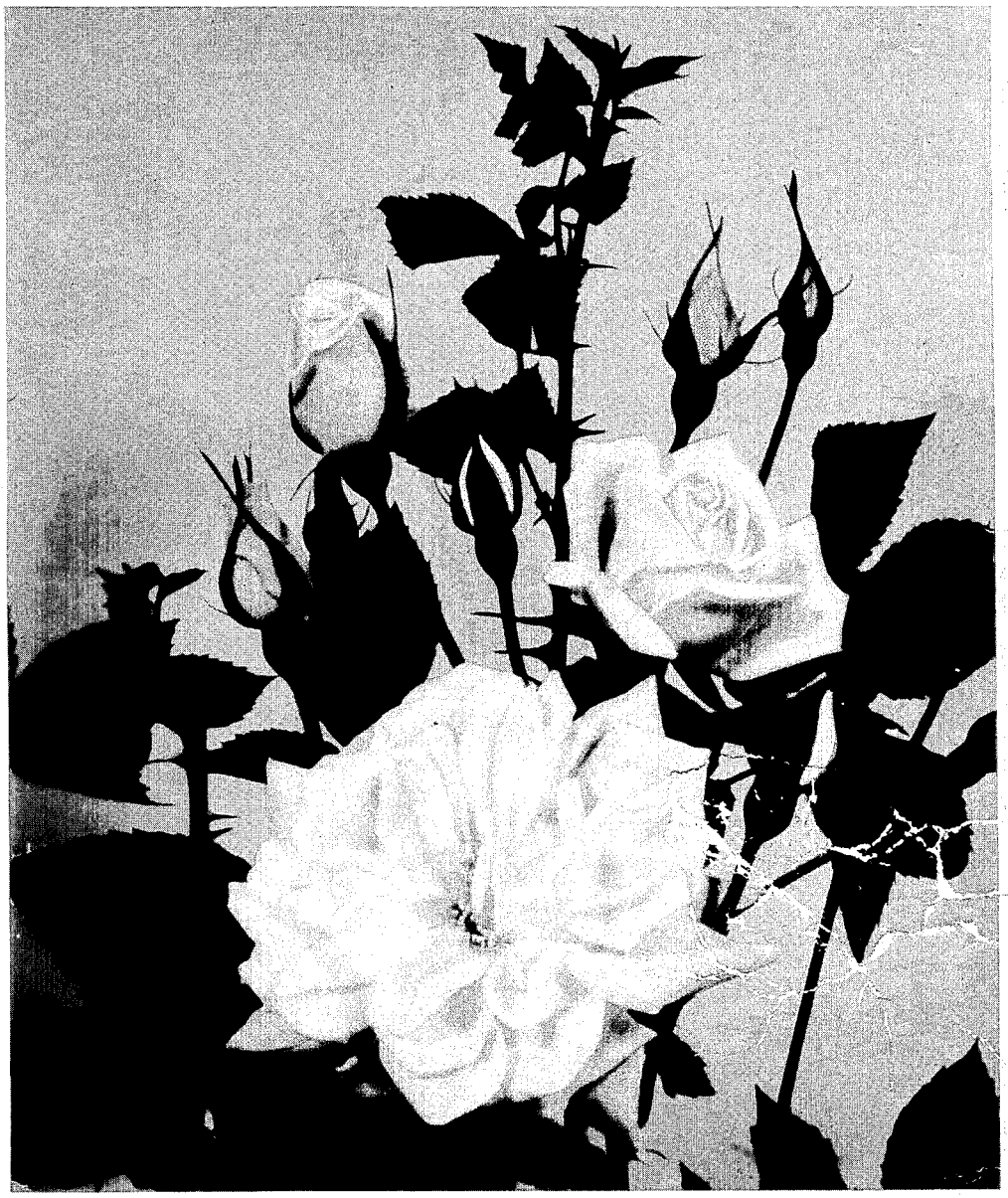
Inventor
E. S. Boerner
By: Robert Cobb
Attorney Patented Apr. 3, 1951

Plant Pat. 1,011

BEST AVAILABLE COPY

UNITED STATES PATENT OFFICE 1,011

ROSE PLANT

Eugene S. Boerner, Newark, N. Y., assignor to Jackson & Perkins Company, Newark, N. Y., a corporation of New York Application February 21, 1950, Serial No. 145,358

1 Claim. (Cl. 47—61)

The present invention relates to a new and distinct variety of rose plant of the large-flowered polyantha class, originated by crossing the variety "Pinocchio" (Plant Patent No. 484) with a golden colored unnamed hybrid tea seedling.

The primary objective in making this deliberate cross was to produce a true yellow form of the "Pinocchio" variety. This objective was achieved with marked success in that it resulted in a new variety of true yellow floribunda blooms, combined with the foliage and plant habits of the hybrid tea parent which were bred into the new variety, and which are particularly evidenced by such very desirable and outstanding characteristics as steady blooming quality, and the straight neck of the flo[illegible]

This combinatio[illegible]acteristics of the new variety is unique [illegible] plant of the large-flowered polyanth[illegible]

Asexual [illegible] this new variety by budding [illegible] York, and at Pleasanton, Ca[illegible] the foregoing characteristic[illegible] cone t[illegible]e and are fixed and transmitted through succe[illegible]ing propagations.

In the accompanying drawing are shown specimens of the new variety, with the flowers at different stages of development from small bud to full-open bloom.

The following is a detailed description of the new variety, with color terminology in accordance with Ridgway's Color Standards and Nomenclature:

Parentage: Seedling.
- *Seed parent.*—"Pinocchio."
- *Pollen parent.*—Golden unnamed hybrid tea seedling.

Classification:
- *Botanic.*—Large-flowered polyantha.
- *Commercial.*—Floribunda.

*Flower*

Observations made in greenhouse in the afternoon of January 10, 1950.

Blooming habit: Recurrent—continuous.

Bud:
- *Size.*—Medium.
- *Form.*—Pointed. Is not affected by wet or hot weather.
- *Color.* — When sepals first divide — Pale Greenish Yellow, Plate 5. When petals begin to unfurl—Empire Yellow, Plate 4. When half blown—inside of petals—Lemon Yellow, Plate 4; reverse of petals—Empire Yellow, Plate 4.

- *Sepals.*—Branched, "hood" above bud. Curl back when petals begin to unfurl. Color—inside—Olivine, Plate 32; outside—Cress Green, Plate 31.
- *Calyx.* — Shape — apple. Size — large. Aspect—smooth. Odor when rubbed—none. Color—Cedar Green, Plate 6.
- *Peduncle.* — Length — medium. Aspect—prickly. Color — Bice Green, Plate 17. Strength—erect; slender.
- *Opening.*—Opens up well. Is not affected by adverse weather conditions.

Bloom:
- *Size.*—Medium. Average size when fully expanded, 3½"–4".
- *Borne.*—Several together.
- *Stems.*— Medium length; strong.
- *Form.*—When first open—globular. Permanence—flattens.
- *Petalage.*—Double (full but open center). Number of petals under normal conditions, 35.
- *Color.*—Center of flower—Pinard Yellow, Plate 4. Outer petals—Sulphur Yellow, Plate 5. Base of petals (aiglet)—Lemon Chrome, Plate 4. Inside of petals—Martius Yellow, Plate 4. Reverse of petals—Sulphur Yellow, Plate 5. General tonality from a distance—Pinard Yellow, Plate 4.
- *Discoloration.*—General tonality at end of first day—Pinard Yellow, Plate 4. Second day—between Pinard Yellow, Plate 4, and Martius Yellow, Plate 4. Third day— Sulphur Yellow, Plate 5.

Petals:
- *Texture.*—Leathery. Is not affected by wet or hot weather.
- *Appearance.*—Inside—satiny; outside—shiny.
- *Form.*—Oval.
- *Arrangement.*—Informal (with "rags" in center). Petaloids in center—few; large.
- *Persistence.*—Drop off cleanly.
- *Fragrance.*—Slight. Nature—"Old Rose perfume" (centifolia).
- *Lasting quality.*—On the plant and as cut flower—long.

Genital organs:
- *Stamens, anthers.*—Medium size; many. Color—Light Cadmium, Plate 4. Arrangement—regular around styles.
- *Stamens, filaments (threads).* — Long. Color—Lemon Yellow, Plate 4.
- *Pollen.*—Color—Apricot Yellow, Plate 4.
- *Styles.*—Loosely separated, uneven length; medium length; thin.

BEST AVAILABLE COPY

*Stigmas.*—Color—Sulphur Yellow, Plate 5.
*Ovaries.*—All enclosed in calyx.

*Plant*

Form: Bush.
Growth: Vigorous; branching.
Foliage: 3–5 leaflets.
*Size.*—Large.
*Quantity.*—Normal.
*Color.*—New foliage: upper side—Oil Green, Plate 5, lightly overcast with Oxblood Red, Plate 1; under side—Cosse Green, Plate 5, overcast with Oxblood Red, Plate 1; serrations Oxblood Red, Plate 1. Old foliage: upper side—Dark Cress Green, Plate 31; underside—Light Elm Green, Plate 17.
*Shape.*—Oval pointed.
*Texture.*—Upper side — leathery. Under side—smooth. Ribs and veins—prominent.
*Edge.*—Serrated (saw toothed).
*Serration.*—Single; large.
*Leaf stem.*—Color—Courge Green, Plate 17. Under side—smooth.
*Stipules.*—Long; slightly bearded.

*Disease resistance.*—Resistant.
Wood:
*New wood.*—Color—Yellowish Oil Green, Plate 5, with overcast of Oxblood Red, Plate 1. Bark—smooth.
*Old wood.*—Color—Cerro Green, Plate 5. Bark—smooth.
Thorns:
*Thorns.*—Quantity—on main stalks from base and on laterals from stalk—many. Form—narrow base; medium length; straight. Color when young—Eugenia Red, Plate 13. Position—irregular.
*Prickles and hairs.*—None.

I claim:

A new and distinct variety of floribunda rose plant, characterized as to novelty by the true yellow color of its flowers, by their straight necks, by the steady blooming quality, and by the general plant and foliage characteristics of its pollen parent, substantially as shown and described.

EUGENE S. BOERNER.

No references cited.